United States Patent
Neef et al.

[11] Patent Number: 5,446,035
[45] Date of Patent: Aug. 29, 1995

[54] 20-METHYL-SUBSTITUTED VITAMIN D DERIVATIVES

[75] Inventors: Günter Neef; Andreas Steinmeyer; Gerald Kirsch; Katica Schwarz; Ruth Thieroff-Ekerdt; Herbert Wiesinger; Martin Haberey, all of Berlin, Germany

[73] Assignee: Schering Aktiengesellschaft, Berlin and Bergkamen, Germany

[21] Appl. No.: 307,081

[22] Filed: Sep. 16, 1994

Related U.S. Application Data

[63] Continuation of Ser. No. 988,262, Dec. 14, 1992, abandoned.

[30] Foreign Application Priority Data

Dec. 13, 1991 [DE] Germany .................. 41 41 746.1

[51] Int. Cl.⁶ .................................. C07C 401/00
[52] U.S. Cl. .................................. 514/167; 552/653
[58] Field of Search .................. 552/653; 514/167

[56] References Cited

PUBLICATIONS

Brown et al., "New active analogues of vitamin D with low calcemic activity", *Kidney International Supplement*, vol. 38, Supplement 29 (1990), pp. S-22-S-27.
Norman et al., "Structure-Function Studies of the Side Chain of 25-Hydroxyvitamin D₃", *The Journal of Biological Chemistry*, vol. 254, No. 22 (Nov. 25, 1979), pp. 1445-1449.
Johnson et al., "Studies on Vitamin D (Calciferol) and Its Analogues. 10. Side-Chain Analogues of 25-Hydroxyvitamin D₃", *Journal of Medicinal Chemistry*, vol. 20, No. 1 (1977), pp. 5-11.

*Primary Examiner*—Howard T. Mars
*Assistant Examiner*—Kimberly J. Kestler
*Attorney, Agent, or Firm*—Millen, White, Zelano & Branigan

[57] ABSTRACT

New 20-methyl-substituted vitamin D derivatives of general formula I

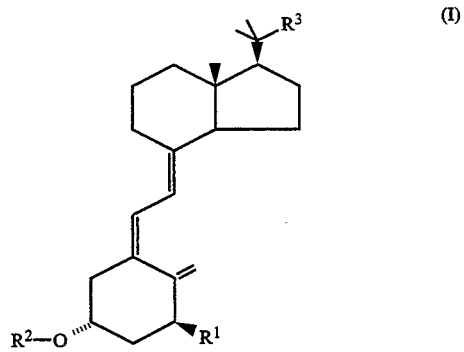

are described
in which $R^1$ means a hydrogen atom, a hydroxy group or an alkanoyloxy group with 1 to 12 carbon atoms or a benzoyloxy group, $R^2$ means a hydrogen atom or an alkanoyl group with 1 to 12 carbon atoms or a benzoyl group and $R^3$ means a saturated or unsaturated, straight-chain or branched hydrocarbon radical with up to 18 C atoms, which optionally contains carbocyclic structures, optionally substituted with one or more hydroxy, oxo, amino group(s) and/or one or more halogen atom(s) as well as optionally exhibits one or more oxygen, sulfur and/or nitrogen atom(s) as a bridging link or links in the hydrocarbon radical, and a process for their production.

Relative to calcitriol, the new compounds exhibit a greatly improved induction of cell differentiation (HL-60) and are suitable for the production of pharmaceutical agents.

7 Claims, No Drawings

20-METHYL-SUBSTITUTED VITAMIN D DERIVATIVES

This application is a continuation, of application Ser. No. 07/988,262, filed Dec. 14, 1992 now abandoned.

BACKGROUND OF THE INVENTION

This invention relates to 20-methyl-substituted vitamin D derivatives of general formula I

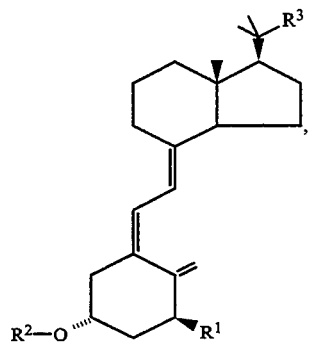

in which $R^1$ means a hydrogen atom, a hydroxy group or an alkanoyloxy group with 1 to 12 carbon atoms or a benzoyloxy group, $R^2$ means a hydrogen atom or an alkanoyl group with 1 to 12 carbon atoms or a benzoyl group and $R^3$ means a saturated or unsaturated, straight-chain or branched hydrocarbon radical, e.g., alkyl, alkenyl or alkynyl, with up to 18 C atoms, which optionally contains either within the side chain or substituted thereon, carbocyclic structures, e.g., $C_{3-10}$-cycloalkyl or $C_{3-10}$-cycloalkenyl, preferably having 1-2 double bonds, said hydrocarbon radical being optionally substituted with one or more hydroxy, oxo, amino group(s) and/or one or more halogen atom(s) as well as optionally exhibits one or more oxygen, sulfur and/or nitrogen atom(s) as a bridging link or links in the hydrocarbon radical, a process for their production, pharmaceutical preparations which contain these compounds as well as their use for the production of pharmaceutical agents.

The alkanoyloxy or alkanoyl groups with 1 to 12 carbon atoms possible for radicals $R^1$ or $R^2$ are derived especially from saturated carboxylic acids. These radicals can be cyclic, acyclic, carbocyclic or heterocyclic and all optionally also unsaturated. The preferred radicals are derived from $C_1$ to $C_9$, especially $C_2$ to $C_5$, alkanecarboxylic acids, such as, for example, acetyl(oxy)-, propionyl(oxy)-, butyryl(oxy)-.

As radicals $R^3$, all side chains described for vitamin D activity are suitable which can be seen, for example, from the following patents and patent applications:

U.S. Pat. No. 4,927,815 (May 22, 1990, De Luca et al.)
U.S. Pat. No. 4,906,785 (Mar. 6, 1990, Baggiolini et al.)
U.S. Pat. No. 4,897,387 (Jan. 30, 1990, Ikekawa et al.)
U.S. Pat. No. 4,866,048 (Sep. 12, 1989, Calverley et al.)
U.S. Pat. No. 4,857,518 (Aug. 15, 1989, De Luca et al.)
U.S. Pat. No. 4,851,401 (Jul. 25, 1989, De Luca et al.)
EP-A-0 421 561 (Kirsch et al.)
EP-A-0 441 467 (Neef et al.)
EP-A-0 450 743 (Neef et al.)

Preferred radicals $R^3$ are the following chains mentioned with respect to the structural formula:

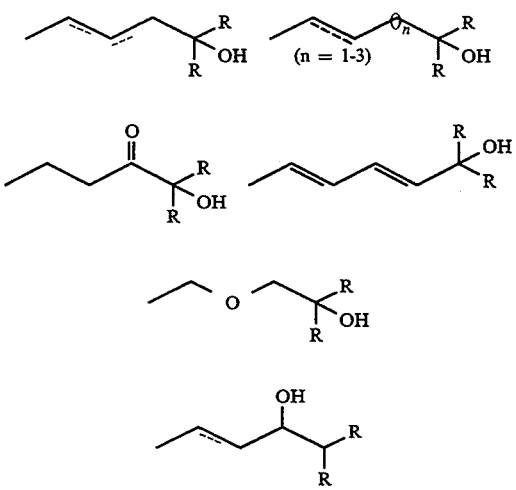

$R = C_1C_4$ alkyl, $C_1-C_4$ hydroxyalkyl, $C_1-C_4$-alkoxy.

In particular, the following compounds according to the invention can be mentioned:

1α,25-dihydroxy-20,26,27-trimethyl-23-oxa-vitamin $D_3$;

1(S),3(R)-dihydroxy-20-(5-hydroxy-5-methyl-hexa-1E,3E-dien-1-yl)-20-methyl-9,10-secopregna-5Z,7E,10(19)-triene;

1α,25-dihydroxy-20-methyl-vitamin $D_3$;

1α,25-dihydroxy-20-methyl-24-homo-vitamin $D_3$;

1α,24(S)-dihydroxy-20-methyl-vitamin $D_3$;

1α,25-dihydroxy-20-methyl-23-oxa-vitamin $D_3$;

1α,24(R),25-trihydroxy-20-methyl-vitamin $D_3$;

1α,24(S),25-trihydroxy-20-methyl-vitamin $D_3$;

1α,25-dihydroxy-20-methyl-24-oxo-vitamin $D_3$;

(5Z,7E)-(1S,3R)-20-methyl-20-vinyl-9,10-secopregna-5,7,10(19)-triene-1,3-diol;

(5Z,7E)-(1S,3R)-20-ethyl-20-methyl-9,10-secopregna-5,7,10(19)-triene-1,3-diol;

(5Z,7E)-(1S,3R)-20-hydroxymethyl-20-methyl-9,10-secopregna-5,7,10(19)-triene-1,3-diol;

1α,25-dihydroxy-20-methyl-23-dehydro-vitamin $D_3$; or

1α,25-dihydroxy-20,26,27-trimethyl-23-dehydro-vitamin $D_3$.

Natural vitamins $D_2$ and $D_3$ (cf. general formula VI) are biologically inactive in themselves and are converted to their biologically active metabolites only after hydroxylation in 25-position in the liver or in 1-position in the kidney. One of the actions of vitamins $D_2$ and $D_3$ involves stabilizing the plasma-$Ca^{++}$ and plasma-phosphate levels; these compounds counteract a drop of the plasma-$Ca^{++}$ level.

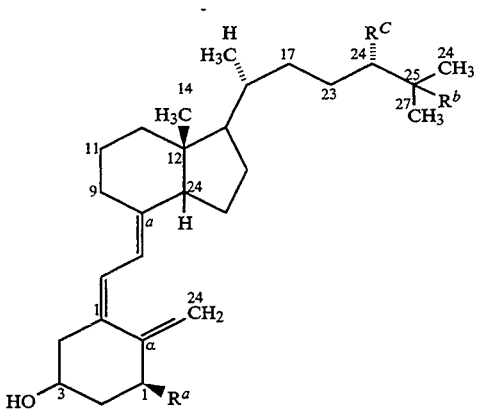

Ergocalciferol: $R^a=R^b=H$; $R^c=CH^3$; Vitamin $D_2$ Double bond C-22/23
Cholecalciferol: $R^a=R^b=R^c=H$ Vitamin $D_3$
25-Hydroxycholecalciferol: $R^a=R^c=H$; $R^b=OH$
1α-Hydroxycholecalciferol: $R^a=OH$; $R^b=R^c=H$
1α,25-dihydroxycholecalciferol: $R^a=R^b=OH$; $R^c=H$ Calcitriol In addition to their pronounced effect on the calcium and phosphate metabolism, vitamins $D_2$ and $D_3$ and their synthetic derivatives also have proliferation-inhibiting and cell-differentiating actions (H. F. De Luca, "The Metabolism and Function of Vitamin D" in Biochemistry of Steroid Hormones, Editors H. L. J. Makin, 2nd Edition, Blackwell Scientific Publications 1984, pp. 71–116).

But in vitamin D use, overdose phenomena can occur (hypercalcemia).

Hydroxylated 1α-cholecalciferols in 24-position are known from DE-AS-25 26 981; they have a lower toxicity than the corresponding nonhydroxylated 1α-cholecalciferol. The hydroxylated compounds show a selective activation of the intestinal calcium absorption and a weaker bone absorption action than 1α-cholecalciferol.

The 24-hydroxy-vitamin D analogs described in international patent application WO 87/00834 can be used for the treatment of disorders in humans and animals caused by abnormal cell proliferation and/or cell differentiation.

For various 1,25-dihydroxy-homo-vitamin D derivatives, a dissociation relative to the properties of bone absorption action and HL-60 cell differentiation has already recently been mentioned by De Luca. The bone absorption action in vitro is here a direct measurement for the calcium immobilization in vivo.

The new vitamin D derivatives of general formula I are distinguished relative to the already known side chain-modified compounds with vitamin D activity by an additional methyl group on carbon atom 20. In this way, the position C-20 loses the nature of an asymmetric center.

In addition to the thus caused simplifications in synthesis and purification of intermediate and end products, new compounds result which exhibit surprisingly high biological activity. Measured by the calcitriol standard (1α,25-dihydroxycholecalciferol, or "1α,25-dihydroxyvitamin $D_3$"), the substances according to the invention with comparable affinity for the calcitriol receptor show an induction of the cell differentiation (HL-60) improved by several powers of ten and are therefore suitable in a special way for treating diseases which are characterized by hyperproliferation and impaired cell differentiation, such as, e.g., hyperproliferative diseases of the skin (psoriasis and acne: J. Invest. Dermatol., Vol. 92, No. 3, 1989) and malignant tumors (leukemia, colon cancer, breast cancer).

In an especially preferred embodiment of the invention, calcitriol receptors are detected before the treatment in the target organ.

In addition, the new compounds can of course also be used in a similar way as the known vitamin D derivatives for treatment of disorders of the calcium metabolism, for immunomodulation and for slowing down the aging of the skin.

Upon further study of the specification and appended claims, further objects and advantages of this invention will become apparent to those skilled in the art.

The vitamin D activity of the compounds according to the invention is determined by the calcitriol receptor test. It is performed by using a specific receptor protein from the intestines of young hogs. Receptor-containing binding protein is incubated with $^3$H-calcitriol ($5 \times 10^{-10}$ mol/l) in a reaction volume of 0.270 ml in the absence and in the presence of test substances for two hours at 4° C. in a test tube. For separation of free and receptor-bound calcitriol, a charcoal-dextran absorption is performed. For this purpose, 250 μl of a charcoal-dextran suspension is added to each test tube and incubated at 4° C. for 20 minutes. Then, the samples are centrifuged at 10,000×g for 5 minutes at 4° C. The supernatant is decanted and, after 1 hour of equilibration in picofluorine 15 TM, measured in a β-counter.

The competition curves obtained with various concentrations of the test substance as well as of the reference substance (unlabeled calcitriol) at constant concentration of the labeled reference substance ($^3$H-calcitriol) are plotted in relation to one another and a competition factor (KF) is determined.

This factor is defined as a quotient of the concentrations of the respective test substance and the reference substance, which are necessary for 50% competition:

$$KF = \frac{\text{Concentration of test substance at 50\% competition}}{\text{Concentration of reference substance at 50\% competition}}$$

The lower the KF value, the more effective the compound is at inducing cell differentiation. A value of KF>1 means that the compound bins more weakly than calcitriol, a value of KF=1 means that the compound binds as strong as calcitriol, and a value of KF<1 means that the compound binds more strongly than calcitriol.

Accordingly, 1(S),(3R)-dihydroxy-20-(5-hydroxy-5-methyl-hexa-1E,3E-dien-1-yl)-20-methyl-9,10-seco-pregna-5Z,7E,10(19)-triene, 1α,25-dihydroxy-20-methyl-23,24-dihydro-vitamin $D_3$ and 1α,25-dihydroxy-20,26,27-trimethyl-23-oxa-vitamin $D_3$ have KF values of 3.4, 0.8 and 1.6, respectively.

The greatly improved induction of cell differentiation by the new compounds is shown in the test described below.

It is known in the literature (Mangelsdorf, D. J. et al., J. Cell. Biol. 98: 391–398 (1984)) that the treatment of human leukemia cells (promyelocyte cell line HL-60, available, e.g., from the ATCC, Rockville, Md.) in vitro with calcitriol induces the differentiation of the cells to macrophages.

HL-60 cells are cultivated in tissue culture medium (RPMI - 10% fetal calf serum) at 37° C. in an atmosphere of 5% $CO_2$ in air.

For substance testing, the cells are centrifuged and $2.8 \times 10^5$ cells/ml are suspended in phenol red-free tissue culture medium. The test substances are dissolved in ethanol and diluted with tissue culture medium without phenol red to achieve the desired concentration. The diluted test substances are mixed with the cell suspension in a ratio of 1:10 and 100 µl each of this cell suspension mixed with substance is pipetted in a depression of a 96-hole plate. As a control, a cell suspension is prepared similarly, but only with the solvent.

After incubation for 96 hours at 37° C. in 5% $CO_2$ in air, 100 µl of an NBT-TPA solution (nitro blue tetrazolium (NBT), end concentration in the batch of 1 mg/ml, tetradecanoylphorbolmyristate-13-acetate (TPA), end concentration in the batch of $2 \times 10^{-7}$ mol/l) is pipetted into each depression of the 96-hole plate containing the cell suspension.

The intracellular oxygen radical ($O_2^{2-}$) release is stimulated by TPA by incubation over 2 hours at 37° C. and 5% $CO_2$ in air; NBT is reduced by the oxygen radical to insoluble formation in the cells differentiated to macrophages.

For completion of the reaction, the depressions of the 96-hole plate are suctioned off, and the adherent cells are fixed by adding methanol and dried after fixation.

To dissolve the formed intracellular formazan crystals, 100 µl of potassium hydroxide (2 mol/l) and 100 µl of dimethylsulfoxide are pipetted into each depression and ultrasonically irradiated for 1 minute. The concentration of formazan is spectrophotometrically measured at 650 nm.

As a measurement for the differentiation induction of HL 60 cells to macrophages, the concentration of formed formazan is determined. The relative activity of the test substance in inducing differentiation is represented by the ratio, $ED_{50}$ test substance/$ED_{50}$ calcitriol. The compounds according to the invention prove thereby more effective by several powers of ten compared to calcitriol ($ED_{50}$ 1(S),3(R)-dihydroxy-20-(5-hydroxy-5-methyl-hexa-1E,3E-dien-1-yl)-20-methyl-9,10-secopregna-5Z,7E,10(19)-trien/$ED_{50}$ Calcitriol $\sim 10^{-3}$).

For determination of lymphocyte proliferation, human peripheral blood mononuclear cells were prepared from venous blood treated by citrate by density gradient centrifugation, seeded at a density of $5 \times 10^4$/cells$\times 200$ µl into microtiter well plates and cultured in RPMI 1640 tissue culture medium in the presence of 10% fetal calf serum. At the time of seeding, cells were treated with phytohemagglutinin (PHA) 5 µg/well. The test compound was added at the same time as PHA in various concentration. Lymphocyte proliferation was determined 96 hours after stimulation by incorporation of [$^3$H]-thymidine. For that, [$^3$H]-thymidine (0.2 µCi/well) was added for the last 6 hours of culture, then medium and cells were filtrated through a glass fiber filter. Radioactivity of the filters were determined in a β-counter.

For determination of IL-2 secretion, human peripheral blood mononuclear cells were prepared as above, seeded at a density of $2 \times 10^6$ cells/well$\times 200$ µl into 24-well-plates and cultured in RPMI 1640 in the presence of 2% fetal calf serum. At the time of seeding, PHA (20 µg/well) and the test compound was added. 24 hours after stimulation, cell cultures were harvested, medium separated from cells by centrifugation, and IL-2 concentration in the medium determined by an ELISA based on a polyclonal antibody IL-2.

ZK 157202 (1α,25-dihydroxy-20-methyl-23,24-dehydrovitamin $D_3$) inhibited lymphocyte proliferation by 50% at a concentration of $1.3 \times 10^{-11}$ mol/l. For comparison, 1,25-dihydroxy-vitamin $D_3$ inhibited lymphocyte proliferation by 50% at a concentration of $4.4 \times 10^{-10}$ mol/l.

ZK 157202 inhibited IL-2 secreted by stimulated lymphocytes into the medium starting at a concentration range about the same as for calcitriol. Maximal inhibition (30% of untreated control cultures) was achieved at a concentration of $10^{-6}$ mol/l.

Due to the potent inhibitory effect of the compounds according to the invention on lymphocyte proliferation and IL-2 synthesis, the compounds will be suited for the treatment of disorders of the immune system, like atopic diseases (atopic dermatitis, asthma, hay fever), autoimmune diseases including diabetes mellitus and transplant rejection. Recently, evidence was presented that infection with the human immunodeficiency virus (HIV type 1 and 2) resembles an autoimmune disease, or an infection with a superantigen. Both theories have in common that initially there is a stimulation of the immune system in AIDS. The disclosed compounds, therefore, will have therapeutic activity in HIV infection.

1,25-dihydroxyvitamin $D_3$ was shown not only to inhibit lymphocyte proliferation and Interleukin 2 synthesis, but also the production of other proinflammatory cytokines in a vitamin D receptor-mediated fashion. The compounds according to the invention, as potent vitamin D receptor agonists, therefore, will also be suited for the treatment of inflammatory disorders like arthritis, colitis ulcerosa ileitis terminalis.

In the treatment of autoimmune diseases, transplant rejections and AIDS, combination of the new compounds with other immunosuppressants like cyclosporin A and FK 506 will be advantageous.

This invention thus relates also to pharmaceutical preparations which contain at least one compound according to general formula I together with a pharmaceutically compatible vehicle. The compounds can be formulated as solutions in pharmaceutically compatible solvents or as emulsions, suspensions or dispersions in suitable pharmaceutical solvents or vehicles, or as pills, tablets, or capsules, which contain solid vehicles as known in the art. For a topical use, the compounds are formulated advantageously as creams or ointments, or in a similar pharmaceutical agent form suitable for topical use. Each such formulation can also contain other pharmaceutically compatible and nontoxic auxiliary agents, such as, e.g., stabilizers, antioxidants, binders, dyes, emulsifiers or flavoring substances. The compounds are advantageously administered by injection or intravenous infusion of suitable sterile solutions or as oral dosage by the alimentary tract or topically in the form of creams, ointments, lotions or suitable transdermal plasters, as is described in EP-A-0387 077.

A daily dose, e.g., is at 0.1 µg/patient/day - 1000 µg (1 mg)/patient/day preferably, 1.0 µg/patient/day - 500 µg/patient/day.

The invention further relates to the use of the compounds according to formula I for production of pharmaceutical agents.

The production of the compounds of general formula I takes place according to the invention in that a compound of general formula II

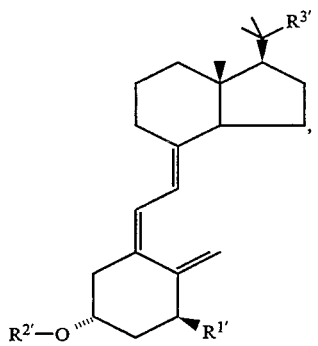

(II)

in which

R$^{1'}$ means a hydrogen atom or a protected hydroxy group;

R$^{2'}$ means an alkali-stable hydroxy protecting group; and

R$^{3'}$ has the same meaning as R$^3$ in the finally desired compound of general formula I, wherein optionally present hydroxy groups are protected, in R$^{3'}$ and R$^{1'}$ by, e.g., alkali-stable protecting groups as in R$^{2'}$.

is converted by cleavage of the present hydroxy protecting groups and optionally by partial or complete esterification of the hydroxy group(s) to a compound of general formula I.

The alkali-stable hydroxy protecting groups are preferably a tert-butyldimethylsilyl group, a tert-butyldiphenylsilyl group, or other tertiary silyl groups. The cleavage of the tertiary silyl groups is possible, e.g., by using tetra-n-butylammonium fluoride.

After the cleavage of the hydroxy protecting group, free hydroxy groups can optionally be esterified. The esterification of the various free hydroxy groups can take place according to usual processes, partially or completely, using the appropriate carboxylic acid halide (halide=chloride, bromide) or carboxylic acid anhydride.

The production of the initial compounds of general formula II according to the invention starts from the known aldehydes of general formula III

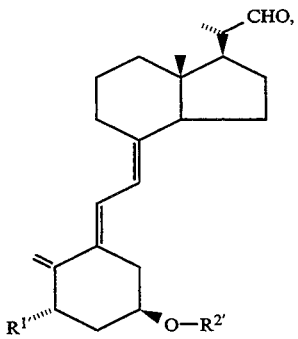

(III)

in which R$^{1'}$ and R$^{2'}$ have the meaning indicated in general formula II (M. J. Calverley, Tetrahedron 43, 4609, 1987; G. Neef et al., Tetrahedron Lett. 1991, 5073).

Their α-alkylation in the usual way produces the dimethylated aldehydes of general formula IV, which then are converted in an also known way by triplet-sensitized photoisomerization to the central intermediate compounds of general formula V

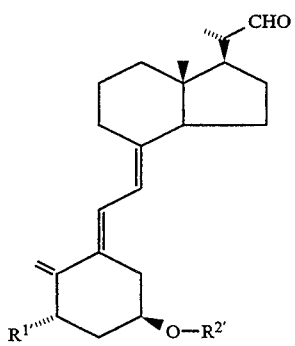

(IV)

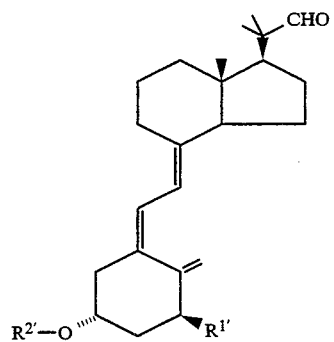

The methylation is performed, e.g., with iodomethane or dimethylsulfate in the presence of a base (e.g., alkali hydroxides, hydrides, amides) in an aprotic solvent, such as tetrahydrofuran, diethyl ether, hexane, ethylene glycol dimethyl ether or toluene, optionally by adding a tetraalkylammonium salt as a phase transfer catalyst.

By irradiation with ultraviolet light in the presence of a so-called "triplet sensitizer" (in the context of this invention, anthracene preferably is used for this purpose), the compounds of general formula IV can be converted to the compounds of general formula V. By cleavage of the π-bond of the 5,6-double bond, rotation of the A-ring by 180° around the 5,6-single bond and reestablishing the 5,6-double bond, the stereoisomerism on the 5,6-double bond is reversed.

Radical R$^{3'}$ is introduced by coupling an aldehyde of general formula V with a precursor of R$^{3'}$ suitable for coupling. This happens analogously to known processes; the experimental performance of these processes is found, for example, in M. J. Calverley, Tetrahedron 43,4609,1987; G. Neef and A. Steinmeyer, Tetrahedron Lett. 1991, 5073; int. patent application WO 91/00855, DE-A-39 33 034 and DE-A-40 11 682. As examples, there can be mentioned: reaction of aldehyde V with a Wittig reagent or reduction of the aldehyde to alcohol and its chain lengthening by reaction with a suitable ω-halogen compound.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 41 41 746.1, are hereby incorporated by reference.

EXAMPLES

Example 1

1α,25-Dihydroxy-20,26,27-trimethyl-23-oxa-vitamin $D_3$ a. A solution of 4.5 g of 1(S)-(tert-butyldimethylsilyloxy)-3(R)-(tert-butyldiphenylsilyloxy)-20(S)-formyl-9,10-secopregna-5E,7E,10(19)-triene in 40 ml of abs. THF is instilled in a suspension of 213 mg of sodium hydride (80% in oil) in 42 ml of abs. THF under ice cooling. After adding 1.18 ml of iodomethane, it is stirred for 2 hours at room temperature, then poured in water and extracted with ethyl acetate.

The crude product obtained after the concentration by evaporation is taken up in 400 ml of toluene and after adding 432 mg of anthracene and 0.2 ml of triethylamine, it is irradiated for 20 minutes at room temperature in a fumigator (pyrex glass) with a mercury high-pressure lamp (Philips HPK 125). After the concentration by evaporation of the reaction solution, the residue is chromatographed on silica gel with hexane/ethyl acetate and 2.38 g of 1(S)-(tert-butyldimethylsilyloxy)-3(R)-(tert-butyldiphenylsilyloxy)-20-formyl-20-methyl-9,10-secopregna-5Z,7E,10(19)triene is obtained as colorless oil.

$^1$H-NMR (CDCl$_3$, 300 MHz): δ=0.52 ppm (s,3H,H-18); 4.23 (m, 1H,H-3); 4.46 (m,1H,H-1); 4.85 and 5.21 (m,1H,H-19 each); 6.04 and 6.11 (d, J=11 Hz; 1H,H-6 and H-7 each), 9.66 (d,1H, CHO).

b. First a solution of 1.41 g of CeCl$_3$ (heptahydrate) in 25 ml of methanol is instilled in a solution of 2.35 g of the aldehyde, obtained under a, in 25 ml of THF and 25 ml of methanol. After adding 91 mg of sodium borohydride, it is stirred for 90 minutes at 25° C., then poured in water and extracted with ethyl acetate. Chromatography on silica gel with hexane/ethyl acetate yields 1.86 g of 1(S)-(tert-butyldimethylsilyloxy)-3(R)(tert-butyldiphenylsilyloxy)-20-hydroxymethyl-20-methyl-9,10-secopregna-5Z,7E,10(19)-triene as colorless oil.

c. A two-phase system, consisting of 10.1 ml of 25% NaOH, 2.74 ml of bromoacetic acid tert-butyl ester, 1.67 g of the alcohol, obtained under b, in 25 ml of toluene and 48 mg of tetrabutylammonium hydrogen sulfate, is stirred for 6 hours at 50°-60° C. After the cooling, it is diluted with toluene, the toluene phase is separated, the latter is washed with water, dried on Na$_2$SO$_4$ and concentrated by evaporation. After chromatography on silica gel with hexane/ethyl acetate, 830 mg of 1(S)-(tert-butyldimethylsilyloxy)-3(R)-(tert-butyldiphenylsilyloxy)-20-(tert-butoxycarbonylmethoxymethyl)-20-methyl-9,10-secopregna-5Z,7E,10(19)-triene is obtained as yellowish oil.

d. The magnesium-organic compound is produced in the usual way from 490 mg of magnesium (chips) and 1.5 ml of bromoethane in 13 ml of abs. THF. After adding, drop by drop, 810 mg of the tert-butyl ester obtained under c, it is stirred for 3 hours at room temperature. The reaction solution is poured in NH$_4$Cl solution for working up and extracted with ethyl acetate.

e. The oily crude product obtained after concentration by evaporation is dissolved in 15 ml of THF and after adding 1.3 g of tetrabutylammonium fluoride, it is stirred for 2 hours at 50° C. After the usual working up, it is chromatographed on neutral aluminum oxide with hexane/ethyl acetate. By crystallization of the main fraction of diisopropyl ether/ethyl acetate, 145 mg of the title compound of melting point 146°-148° C. is obtained.

$^1$H-NMR (CDCl$_3$, 300 MHz): δ=0.63 ppm (s,3H); 0.92 (s,3H); 1.00 (s,3H); 3.16 (s,2H); 3.23 (AB-q,J-9 and 7 Hz,2H); 4.23 (m,1H); 4.43 (m,1H); 4.98 (m,1H); 5.32 (m, 1H); 5.90 (d,J=11 Hz,1H); 6.38 (d,J=11 Hz,1H).

Example 2

1(S),3(R)-Dihydroxy-20-(5-hydroxy-5-methyl-hexa-1E,3E-dien-1-yl)-20-methyl-9,10-secopregna-5Z,7E,10(19)-triene The reaction sequence described in PCT application WO 91/00855 was performed with 2.12 g of the aldehyde obtained under example 1a. After Wittig reaction with methoxycarbonyl-triphenylphosphorane, reduction with diisobutylaluminum hydride, oxidation with pyridinium dichromate, renewed Wittig olefination with methoxycarbonyl-triphenylphosphorane, reaction of the obtained ester with methyllithium and protecting group cleavage with tetrabutylammonium fluoride, 600 mg of the title compound was obtained as colorless oil.

$[α]_D$ −65.5° (CDCl$_3$, c=0.525).

$^1$H-NMR (CDCl$_3$, 300 MHz): δ=0.57 ppm (s,3H); 1.04 (s,3H); 1.09 (s,3H); 1.34 (s,6H); 4.23 (m,1H); 4.43 (m,1H); 4.98 (m,1H); 5.32 (m,1H); 5.72 (d,J=15Hz,1H); 5.87 (d,J=10Hz,1H); 5.88 (dd,J=15 and 10 Hz,1H); 6.00 (d,J=11 Hz,1H); 6.19 (dd,J=15 and 10 Hz,1H); 6.37 (d,J=11 Hz,1H).

Example 3

(5Z,7E)-(1S,3R)-20-Hydroxymethyl-20-methyl-9,10-secopregna-5,7,10(19)-triene-1,3-diol By silylether cleavage of the alcohol obtained under example 1b under the conditions of example 1e, the title compound of melting point 183°-185° C. is obtained.

$^1$H-NMR (CDCl$_3$+DMSO-d$_6$, 300 MHz): δ=0.22, 0.46 and 0.58 ppm (3×s, 3H,H-18 and 20-methyl each); 3.73 (m, 1H,H-3); 3.95 (m, 1H,H-1); 4.49 and 4.90 (2×s, 1H,H-19 each); 5.62 and 5.87 (2×d,J=11 Hz, 1H,H-6 and H-7 each).

Example 4

(5Z,7E)-(1S,3R)-20-methyl-20-vinyl-9,10-secopregna-5,7,10(19)-triene-1,3-diol

By reaction of the aldehyde described under example 1a with methylenetriphenylphosphorane and subsequent silylether cleavage according to example 1e, the title compound of melting point 139°-142° C., is obtained $[α]^D$ −23.9° (CHCl$_3$, c=0.255).

$^1$H-NMR (CDCl$_3$, 300 MHz): δ=0.57 ppm (s, 3H,H-18); 1.03 and 1.08 (2×s,3H,20-methyl each); 4.22 (m,1H,H-3); 4.43 (m,1H,H-1); 4.82-4.93 (m,2H,vinyl-CH$_2$); 4.99 and 5.32 (2×s, 1H,H-19 each); 5.93-6.05 (m,2H,H-6 and vinyl-CH); 6.37 (d,J=11 Hz,1H,H-7).

Example 5

(5Z,7E)-(1S,3R)-20-Ethyl-20-methyl-9,10-secopregna-5,7,10(19)-triene-1,3-diol

By homologization of the aldehyde obtained under 1a (e.g., according to M. J. Calverley, Synlett. 1990, 155), subsequent reduction according to example 1b, conversion of the thus obtained alcohol to the corresponding iodide (e.g., according to G. L. Lange and C. Gottardo, Synth. Commun. 1990, 20, 1473), reduction of the iodide with LiAlH$_4$ in THF and subsequent silylether cleavage, the title compound is obtained.

$^1$H-NMR (CDCl$_3$, 300 MHz): δ=0.64 ppm (s,3H,H-18); 0.87 and 9.93 (2×s, 3H,20-methyl each); 4.23 (m,1H-3); 4.42 (m,1H,H-1); 5.01 and 5.34 (2×s, 1H,H-19 each); 6.01 and 6.39 (2×d, J=11 Hz, 1H,H-6 and H-7 each).

Example 6

1α,25-Dihydroxy-20-methyl-23-dehydro-vitamin D$_3$

By homologization of the aldehyde described under 1a (e.g., according to Synlett 1990, 155), Wittig-Horner olefination of the thus obtained homologous aldehyde with dimethylphosphonoacetic acid methyl ester (NaH, THF), reaction of the thus obtained unsaturated ester with methylmagnesium bromide in THF and silylether cleavage, the title compound is obtained as colorless oil.

$^1$H-NMR (CDCl$_3$, 300 MHz): δ=0.64 ppm (s, 3H,H-18); 0.89 and 9.95 (2×s, 3H,20-methyl each); 1.33 (s,6H,25-methyl); 4.23 (m,1H,H-3); 4.43 (m,1H,H-1); 5.00 and 5.33 (2×s, 1H,H-19 each); 5.55–5.72 (m,2H,H-23 and H-24); 6.00 and 6.38 (2×d, J=11 Hz, 1H,H-6 and H-7 each).

Example 7

1α,25-Dihydroxy-20-methyl-24-oxo-vitamin D$_3$

By homologization of the aldehyde described under 1a (e.g., Synlett 1990, 155), Wittig-Horner olefination with diethylphosphono-ethoxyacetic acid ethyl ester (according to W. Grell and H. Machleidt, Liebigs Ann. Chem. 699, 53, 1966), addition of methylmagnesium bromide, enolether cleavage (70% acetic acid) and removal of the silylether protecting groups, the title compound of melting point 141°–144° C. is obtained, [α]$_D$ +14.7° (CHCl$_3$, c=0.505).

$^1$H-NMR (CDCl$_3$, 300 MHz): δ=0.65 ppm (s,3H,H-18); 0.90 and 0.98 (2×s, 3H,20-methyl each); 1.40 (s,6H,25-methyl); 4.23 (m, 1H,H-3); 4.44 (m,1H,H-1); 5.00 and 5.33 (2×broad s, 1H,H-19 each); 6.01 and 6.38 (2×d, J=11 Hz, 1H,H-6 and H-7 each).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 20-Methyl-substituted vitamin D compound of formula I wherein
R$^1$ is a hydrogen atom, a hydroxy group, a C$_1$–C$_{12}$-alkanoyloxy group, or a benzoyloxy group;
R$^2$ is a hydrogen atom, a C$_1$–C$_{12}$-alkanoyl group, or a benzoyl group; and
R$^3$ is a saturated or unsaturated, straight-chain or branched C$_1$–C$_{18}$-hydrocarbon group, which group optionally contains a C$_{3-10}$-cycloalkyl or -cycloalkenyl moiety, said hydrocarbon group optionally being substituted with at least one of hydroxy, oxo, amino or halogen, and in which at least one carbon atom is optionally replaced by an oxygen, sulfur or nitrogen atom.

2. A 20-methyl-substituted vitamin D compound according to claim 1, wherein R$^3$ is R is C$_1$–C$_4$-alkyl, C$_1$–C$_4$-hydroxyalkyl, or C$_1$–C$_4$-alkoxy.

3. 1α,25-dihydroxy-20,26,27-trimethyl-23-oxa-vitamin D$_3$;
1(S),3(R)-dihydroxy-20-(5-hydroxy-5-methyl-hexa-1E,3E-dien-1-yl)-20-methyl-9,10-secopregna-5Z,7E,10(19)-triene;
1α,25-dihydroxy-20-methyl-vitamin D$_3$;
1α,25-dihydroxy-20-methyl-24-homo-vitamin D$_3$;
1α,24(S)-dihydroxy-20-methyl-vitamin D$_3$;
1α,25-dihydroxy-20-methyl-23-oxa-vitamin D$_3$;
1α,25-dihydroxy-20-methyl-23-dehydro-vitamin D$_3$;
1α,25-dihydroxy-20,26,27-trimethyl-23-dehydro-vitamin D$_3$;
1α,24(R),25-trihydroxy-20-methyl-vitamin D$_3$;
1α,24(S),25-trihydroxy-20-methyl-vitamin D$_3$;
1α,25-dihydroxy-20-methyl-24-oxo-vitamin D$_3$;
(5Z,7E)-(1S,3R)-20-methyl-20-vinyl-9,10-secopregna-5,7,10(19)-triene-1,3-diol;
(5Z,7E)-(1S,3R)-20-ethyl-20-methyl-9,10-secopregna-5,7,10(19)-triene-1,3-diol; or
(5Z,7E)-(1S,3R)-20-hydroxymethyl-20-methyl-9,10-secopregna-5,7,10(19)-triene-1,3-diol.

4. A topical pharmaceutical composition, comprising a compound according to claim 1 and a pharmacologically compatible vehicle.

5. A pharmaceutical composition, comprising a compound of claim 1 and a pharmacologically compatible vehicle.

6. A pharmaceutical composition according to claim 5, wherein the vehicle is compatible with oral administration.

7. A pharmaceutical composition according to claim 5, wherein the vehicle is compatible with intravenous administration.

* * * * *